US012746128B2

(12) United States Patent
Srour

(10) Patent No.: US 12,746,128 B2
(45) Date of Patent: Sep. 29, 2026

(54) IMPLANT DEVICE FOR PERFORMING POSTERIOR SPINAL ARTHRODESIS AT A FACET JOINT, AND SYSTEM COMPRISING THE IMPLANT AND ITS POSITIONING TOOL

(71) Applicant: SC MEDICA, Strasbourg (FR)

(72) Inventor: Camille Srour, Strasbourg (FR)

(73) Assignee: SC MEDICA, Strasbourg (FR)

( * ) Notice: Subject to any disclaimer, the term of this patent is extended or adjusted under 35 U.S.C. 154(b) by 0 days.

(21) Appl. No.: 18/837,564

(22) PCT Filed: Jan. 27, 2023

(86) PCT No.: PCT/EP2023/052040
§ 371 (c)(1),
(2) Date: Aug. 9, 2024

(87) PCT Pub. No.: WO2023/156169
PCT Pub. Date: Aug. 24, 2023

(65) Prior Publication Data

US 2025/0143888 A1 May 8, 2025

(30) Foreign Application Priority Data

Feb. 17, 2022 (FR) ....................................... 2201374

(51) Int. Cl.
*A61F 2/44* (2006.01)

(52) U.S. Cl.
CPC .................................. *A61F 2/4405* (2013.01)

(58) Field of Classification Search
CPC .. A61B 17/70; A61F 2/30; A61F 2002/30131; A61F 2/44–2/447
See application file for complete search history.

(56) References Cited

U.S. PATENT DOCUMENTS

| | | | | |
|---|---|---|---|---|
| 6,210,442 | B1 * | 4/2001 | Wing ................... | A61B 17/864 623/17.11 |
| 6,443,990 | B1 | 9/2002 | Aebi et al. | |
| 8,454,623 | B2 * | 6/2013 | Patel ....................... | A61F 2/447 623/17.11 |

(Continued)

FOREIGN PATENT DOCUMENTS

| | | |
|---|---|---|
| EP | 0912147 A1 | 5/1999 |
| FR | 2946245 A1 | 12/2010 |

(Continued)

*Primary Examiner* — Eduardo C Robert
*Assistant Examiner* — Holly Joanna Lane
(74) *Attorney, Agent, or Firm* — Craft Chu PLLC; Andrew W. Chu

(57) ABSTRACT

The implant device for performing posterior spinal arthrodesis at a facet joint is in the form of a flat element of constant thickness. The element has reliefs on each of its faces so as to form an anchor associated with at least one complementary anchor, such as a screw with a diameter greater than the thickness of the element. The complementary anchor can be screwed into the flat element such that at least some of its threads protrude from the faces. The element has a U-shape with a transverse part from which two branches extend. On the proximal side, the free ends of the branches have retention devices, on the inner side of the U so as to permit the screwing and insertion of the screw between the branches.

7 Claims, 3 Drawing Sheets

(56) References Cited

U.S. PATENT DOCUMENTS

| | | | | |
|---|---|---|---|---|
| 8,801,721 | B2 * | 8/2014 | Berry | A61F 2/4611 606/90 |
| 2002/0120334 | A1 * | 8/2002 | Crozet | A61B 17/86 623/17.11 |
| 2002/0138146 | A1 * | 9/2002 | Jackson | A61F 2/4455 623/17.11 |
| 2009/0099661 | A1 * | 4/2009 | Bhattacharya | A61F 2/4455 623/17.11 |
| 2011/0106261 | A1 * | 5/2011 | Chin | A61F 2/4455 606/279 |
| 2011/0230965 | A1 | 9/2011 | Schell et al. | |
| 2014/0114418 | A1 * | 4/2014 | Landry | A61F 2/4455 623/17.16 |
| 2019/0274845 | A1 * | 9/2019 | Ludwig | A61F 2/4611 |
| 2019/0328429 | A1 | 10/2019 | McCormack et al. | |

FOREIGN PATENT DOCUMENTS

| | | | |
|---|---|---|---|
| WO | 9848738 | A1 | 11/1998 |
| WO | 0203895 | A1 | 1/2002 |
| WO | 2012154653 | A1 | 11/2012 |
| WO | 2019016341 | A1 | 1/2019 |

* cited by examiner

IMPLANT DEVICE FOR PERFORMING POSTERIOR SPINAL ARTHRODESIS AT A FACET JOINT, AND SYSTEM COMPRISING THE IMPLANT AND ITS POSITIONING TOOL

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to an implant device for performing posterior spinal arthrodesis at a facet joint, and a system comprising said implant device and its positioning tool.

2. Description of Related Art Including Information Disclosed Under 37 CFR 1.97 and 37 CFR 1.98

Spinal arthrodesis involves fusing two vertebrae to immobilize them.

The posterior route is the easiest, using either an osteosynthesis plate or bar that connects the vertebrae and is fastened thereto by means of pedicle screws, or interbody cages of the type described, for example, in documents US 2011/230965, FR 2 946 245 and WO 02/03895, designed to be placed in the intervertebral space after removal of the vertebral disc.

Two vertebrae can also be immobilized using a posterior approach, by fusing each of the lower articular processes of one vertebra with the upper articular process of the neighboring lower vertebra.

This posterior approach to spinal arthrodesis of a facet joint offers a number of advantages over other commonly used techniques, including less trauma and fewer risks.

However, this technique requires the use of different means from those used in other operating techniques, and in particular cages with different characteristics from those used in the aforementioned documents.

In particular, such a cage needs to have a certain thinness, given the narrowness of the space into which it has to be introduced. As a result, the main difficulty lies in securing that cage.

Implant devices for insertion in a facet joint are already known, in particular the one described in document WO 2012154653, which consists of a wedge-shaped element whose two opposite faces, each intended to come into contact with a facet, having a surface provided with reliefs to anchor it, which is pierced by a multiplicity of holes designed for the development of bone material after deposition of a bone graft, while fastening is achieved by means of two screws, each screwed into a process, obliquely with respect to the median plane of the implant. This implant system remains complex, or more specifically, its implementation is complex.

Already known from document W02019016341 to the present Applicant is an implant in the shape of a flat element of constant thickness, comprising, in order to receive a bone graft, a large central opening which gives it a substantially annular shape, and which device is intended to be inserted into a cavity previously made at the location of the facet joint to be immobilized; said element being D-shaped and comprises a rounded side which constitutes the distal edge for being inserted into said cavity, while the opposite straight proximal edge comprises a means for securing to a holding and positioning tool; while the opposite surfaces of said flat element comprise reliefs which consist of reliefs arranged perpendicularly to the insertion direction, each of the reliefs having a tooth profile with two faces of which one, the face oriented on the side of said proximal edge, is perpendicular or substantially perpendicular to the main plane of said element, while the other face is inclined. The constant thickness prevents expulsion, as might occur when the cage is corner-shaped. And from an implementation point of view, the preparatory work for shaping the cavity is carried out as simply as possible, meaning that in the cavity, the opposing faces are flat and parallel.

In practice, the surgeon prepares the implant site by removing the joint capsule with an instrument called a facet chisel, then uses a rasp to "bleed" the parts opposite the joint space on the facets. This step with the rasp has two purposes: to prepare the pre-existing space, with a boneless but often slightly curved interline, for the straight shape of the implant, and to promote subsequent fusion of the facets through the implant that has bled/revived the facets down to the cancellous bone.

Also known from documents EP0912147 and WO9848738 are interbody implants for use in spinal surgery, designed to be placed in the intervertebral space and not in a facet joint.

These implants take the form of a cage wherein a screw can be journaled, at least part of which has a diameter greater than the thickness of said cage, so as to form anchoring means. Fitting such an implant requires extensive preparatory work, which is difficult to carry out on a facet joint.

In the case of the implant described in EP0912147, the screw is screwed into a threaded annular part located at the periphery of the cage, and therefore with an external diameter greater than the thickness of the cage, which requires special machining of the bone material to accommodate said annular part.

Document WO9848738 proposes a similar implant, with single or double tapered faces to adapt to the characteristics of vertebral bodies.

Although the bone anchoring means of these implants make it possible to dispense with the use of screws, introduced obliquely for example, none of these implants is suitable for posterior spinal arthrodesis at a facet joint, which exhibits installation constraints, because the space into which the implant must be introduced is of reduced dimensions, particularly in terms of thickness.

BRIEF SUMMARY OF THE INVENTION

The aim of the present invention is to remedy the various disadvantages mentioned above, by proposing an implant device, as well as a system comprising said implant and its positioning tool, for performing posterior spinal arthrodesis at a facet joint.

The implant device for performing posterior spinal arthrodesis at a facet joint, according to the invention, takes the form of a flat element of constant thickness, designed to be introduced into a cavity previously made at the location of the facet joint to be immobilized, comprising on each of its faces reliefs forming notches constituting anchoring means, and associated with at least one complementary anchoring means, consisting of a screw with a diameter greater than the thickness of said element, designed to be screwed into said flat element so that at least part of its threads protrude from said faces, and it is characterized in that it is U-shaped, i.e. it comprises a transverse part, from which extend two branches separated by a gap, and where said transverse part constitutes the distal edge for introduction into said cavity, while on the proximal side the free ends of said branches each comprise, on the inner side of the U, retention means capable of enabling said screw to be screwed in and inserted between said branches, and which project from each of the inner sides of said branches to extend into said space, without going beyond the thickness of said flat element.

The U-shape of the implant device, i.e. the fact that it is open on the proximal side, and that it does not comprise an annular element for retaining a screw, makes it possible to obtain an element, in addition to being thin, which does not require specific machining.

In addition, the screw axis is coaxial with the implant insertion axis, enabling a percutaneous approach to be envisaged.

The present invention also concerns a system for performing posterior spinal arthrodesis at a facet joint, comprising an implant device and its positioning tool, wherein said implant is in the form of a flat element of constant thickness, intended to be inserted into a cavity previously made at the location of the facet joint to be immobilized, comprising on each of its faces reliefs forming notches constituting anchoring means, and associated with at least one complementary anchoring means, consisting of a screw with a diameter greater than the thickness of said element, designed to be screwed into said flat element so that at least part of its threads protrude from said faces, and it is characterized in that:

- said implant is U-shaped, i.e. it comprises a transverse part, from which two branches extend, and where said transverse part constitutes the distal edge for introduction into said cavity, while on the proximal side the free ends of said branches each comprise, on the inner side of the U, retention means that are able to permit the screwing and insertion of said screw between said branches,
- said positioning tool comprises an assembly of coaxial parts, namely, firstly, a first part, one end of which is able to hold said flat element by holding it by the outside of its branches, secondly, a second part into which said first part is able to slide until the part thereof holding said flat element is extracted; thirdly, also inside said first part, a third part, one end of which is able to be connected to said flat element and to hold said screw facing said branches; and fourthly, inside said third part, a fourth part which consists of a rod, one end of which is configured to engage said screw and to be able to drive it in rotation through an action on the other end.

According to an additional feature of the system according to the invention, the end of the first part, designed to hold the flat element from the outside of its branches, comprises two parallel branches, designed to grip said branches from the outside.

According to another additional feature of the system according to the invention, the branches of the planar element each have a longitudinal guide groove on the outside for the branches of the first part, and in that the bottoms of said grooves and the inside of said branches have complementary reliefs capable of axially immobilizing said element between said branches when the latter are held externally in the second part.

According to a further feature of the system according to the invention, the reliefs consist of bosses.

According to a further feature of the system according to the invention, the third part is tubular in shape, while its end suitable for holding the screw in place consists of a cavity with a round, threaded cross-section.

According to a further feature of the system according to the invention, the tool comprises an additional part, usable in a percutaneous procedure, and integrating all the other parts.

BRIEF DESCRIPTION OF THE SEVERAL VIEWS OF THE DRAWINGS

The advantages and features of the implant device according to the invention, as well as of the system for performing posterior spinal arthrodesis at a facet joint according to the invention, will become clearer from the following description, which refers to the appended drawing, which represents a non-limiting embodiment thereof.

DETAILED DESCRIPTION OF THE INVENTION

Figure 1:
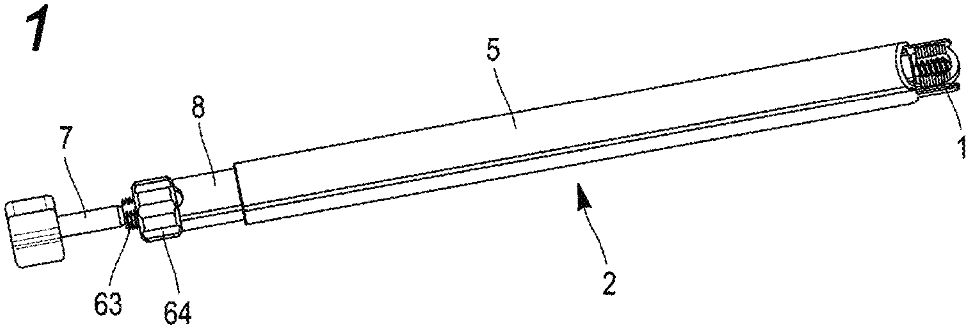
FIG. 1 shows a schematic perspective view of a system according to the invention.

FIG. 1 shows a system 1*b* for performing posterior spinal arthrodesis at a facet joint according to the invention, comprising an implant device 1 and a positioning tool 2 for positioning that implant 1.

Figure 2:
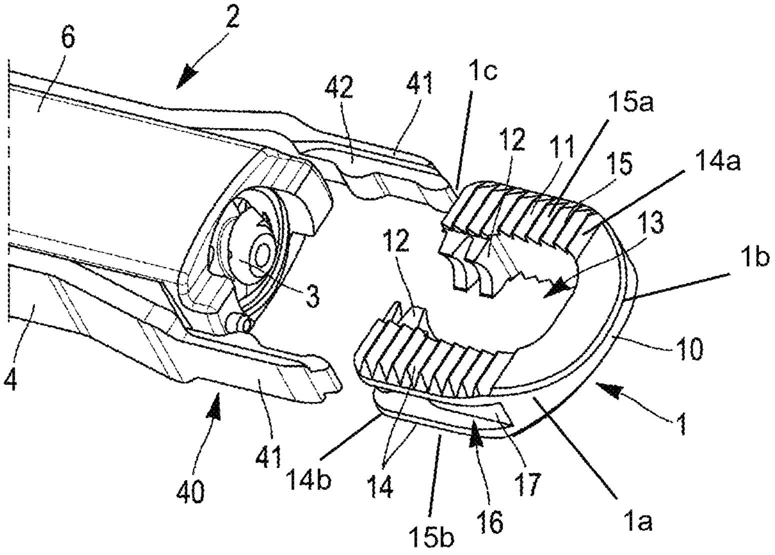
FIG. 2 shows a partial schematic exploded perspective view of the same system, including the implant device according to the invention.
Figure 3:
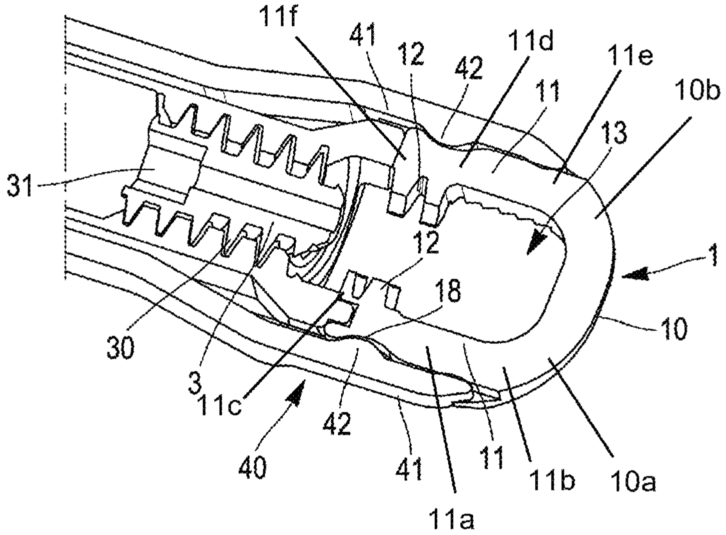
FIG. 3 shows a schematic cross-sectional perspective view in a longitudinal plane of part of the same implant system and device.
Figure 4:
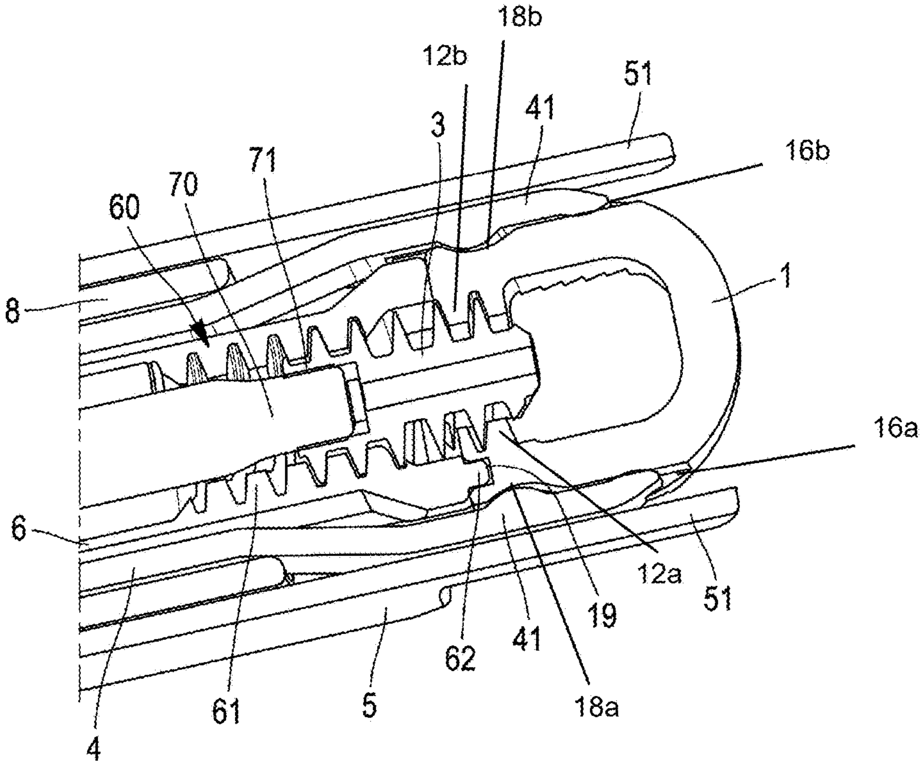
FIG. 4 shows a schematic partial cross-sectional perspective view in a longitudinal plane of the same implant system and device.

Additionally, FIGS. 2, 3 and 4, show that the implant 1 takes the form of a flat element (element 1*a* having a distal edge 1*b* and a proximal side 1*c*) of constant thickness, generally U-shaped, thus comprising a transverse part 10 having a first end 10*a* and a second end 10*b* and constituting the distal edge 1*b*, from which extend two branches 11. The two branches 11 (first branch 11*a* having a first branched end 11*b* and a first free end 11*c*, second branch 11*d* having a second branched end 11*e* and a second free end 11*f*) each have protruding elements 12 (projections 12, first projections 12*a*, second projections 12*b*) on the inside at their free end (first free end 11*c*, second free end 11*f*), forming a thread for screwing in a screw 3, and allowing this screw 3 to occupy the space 13 separating the two branches 11 (first branch 11*a*, second branch 11*d*) once it has been screwed in.

Advantageously, but not in a limiting fashion, the distal edge 1*b* is tapered to facilitate insertion.

The implant device 1 features tooth-shaped reliefs 15 (first reliefs 15*a*, second reliefs 15*b*) on the two outer faces 14 (first outer face 14*a*, second outer face 14*b*) of each of the two branches 11 (first branch 11*a*, second branch 11*d*), to enable it to clamp into the bone material.

On the other hand, the screw 3 has a diameter greater than the thickness of the first branch 11*a* and second branch 11*d* of the implant device 1, more particularly between two faces 14 (first outer face 14*a*, second outer face 14*b*), and more precisely, it is only the threads 30 of the screw 3, or part of it, that protrudes from the faces 14 (first outer face 14*a*, second outer face 14*b*) of the implant device 1.

It can also be seen on these figures that each of the branches 11 (first branch 11*a*, second branch 11*d*) has a longitudinal groove 16 (first longitudinal groove 16*a*, second longitudinal groove 16*b*) on the outside, i.e. on the side opposite that containing the projecting elements 12 (first projections 12*a*, second projections 12*b*), extending along the entire length of the branch 11 (first branch 11*a*, second branch 11*d*). In addition, the bottom 17 of each groove 16 (first longitudinal groove 16*a*, second longitudinal groove 16*b*) features a concave boss 18 (first groove relief 18*a* or second groove relief 18*b*, respectively).

Figure 8:
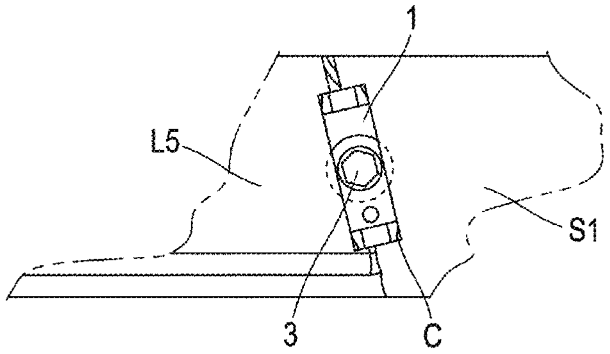
FIG. 8 shows the implant of the same system after placement in a facet joint.

Referring now to FIG. 8, an implant device 1 according to the invention can be seen positioned at the facet joint between vertebrae L5 and SI, the right side of which is shown in part, while the left side, not shown, is similarly equipped.

Prior to insertion, the bone material of both vertebrae is cut away at the facet joint to create a cavity C, shared between the t[wo vertebrae, in this case L5 and SI, extending in the contact plane and of a thickness corresponding to that of implant device 1. The implant device 1 is then inserted into the cavity C.

Once the screw 3 has been screwed in, the thread 30, which is advantageously self-tapping, penetrates the bone material to anchor the implant device 1.

The small dimensions of cavity C, and therefore also those of the implant, can complicate its insertion, particularly in view of the different operations involved, i.e. introduction with impaction, followed by screwing. The positioning tool 2, adapted to the implant device 1, has been designed to facilitate this insertion, forming the system according to the invention.

The positioning tool 2 is thus made up of a multiplicity of elongated, coaxial parts.

The positioning tool 2 thus comprises a first tubular part 4, having a first part back end 4*a* and a first part tip end 4*b*, the first terminal end part 40 holds the implant device 1 by clamping the branches 11. To this end, it comprises two parallel branches 41, each designed to be housed in a groove 16 (first longitudinal groove 16*a*, second longitudinal groove 16*b*) on the implant device 1, in contact with the base or bottom 17, while convex bosses 42 are fitted into the concave bosses 18 (first groove relief 18*a* or second groove relief 18*a*, respectively). The implant device 1 is thus immobilized between the two parallel branches 41, both transversely by the two parallel branches 41 and by the grooves 16 (first longitudinal groove 16*a*, second longitudinal groove 16*b*), and axially through the convex bosses 42 and concave bosses 18 (first groove relief 18*a* or second groove relief 18*a*, respectively).

The positioning tool 2 also features a tubular second part 8, into which the first part 4 can slide axially, and which in its extreme position can constrain the branches 41 to hold the implant device 1.

The positioning tool 2 also features a third tubular part 6, having a third part back end 6*a* and a third part free end 60, and being slidably mounted in the second part 4. Its third part free end 60 has a threaded hole 61 wherein the screw 3 is engaged when in the waiting position.

Optionally, the third part free end 60 of the third part 6 can be fitted with an axially projecting finger 62, designed to engage in a blind hole 19 at the end of a branch 11 of implant device 1, for indexing the two threads of the projections 12 and threaded hole 61.

Figure 6:
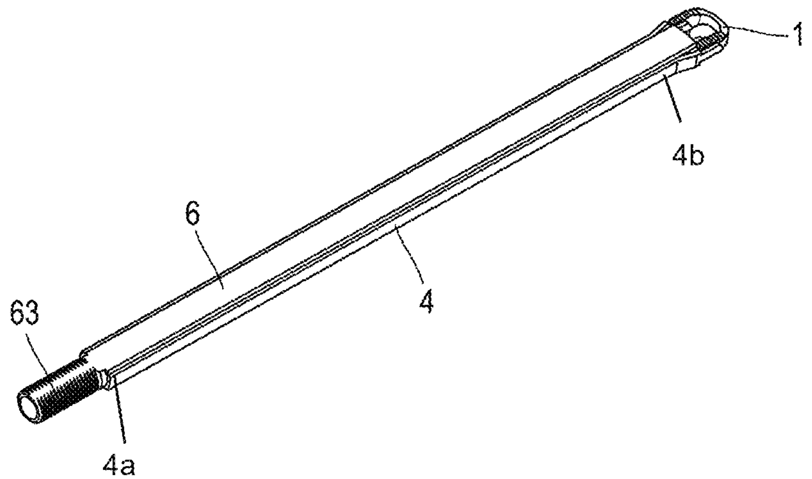
FIG. 6 shows a perspective view of a part of the same system.
Figure 7:
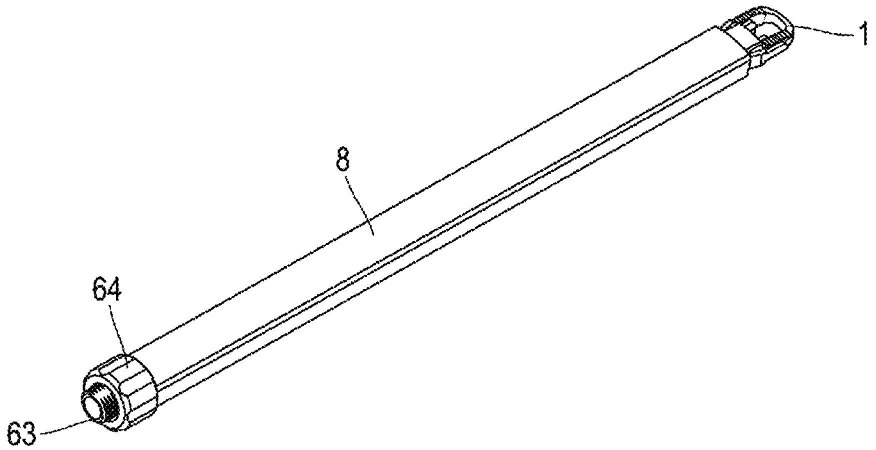
FIG. 7 shows a perspective view of another part of the same system.

It should also be noted that the third part 6 has a threaded portion 63 at the third part back end opposite the one containing the screw 3, onto which a nut 64 is screwed. FIG. 6 shows that tightening the nut 64 on the threaded portion 63 moves the second part 8 on the first part 4, thereby reinforcing the grip of the implant device 1 via the two parallel branches 41.

The positioning tool 2 comprises a fourth part 7, having a back rod end 70*a* and a front rod end 70, and being arranged in the third part 6, which is intended to transmit a screwing torque to the screw 3, and which for this purpose has the front rod end 70 with a male indentation 71 corresponding to the female indentation 31 of the screw 3, which in this case is hexagonal in cross-section.

Figure 5:
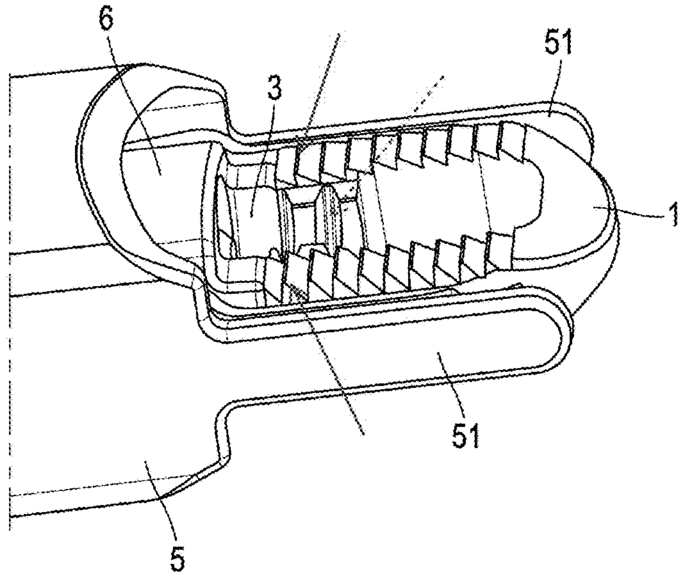
FIG. 5 shows a partial perspective view of the same system.

It should be noted that the version of the system 1*d* described above is the most advanced version, although it is entirely possible that some of the parts may not be necessary depending on the procedure to be performed. This is the case for the additional part 5, which can be used primarily for percutaneous surgery, but which is not required for open surgery. For this purpose, at one end 50, it has two blade-like extensions 51 which, as can be seen more precisely in FIGS. 4 and 5, are positioned against and outside the two parallel branches 41 to hold them in place.

I claim:

1. An implant device for performing posterior spinal arthrodesis of a facet joint, comprises:

an element, having a distal edge, a proximal side opposite said distal edge, a first outer face, a second outer face opposite said first outer face, first reliefs on said first outer face, and second reliefs on said second outer face so as to anchor said element in a cavity of a facet joint by a notched relationship, wherein said element is comprised of:

a transverse part having a first end and a second end opposite said first end, said transverse part being at said distal edge so as to be insertable into the cavity before said proximal side of said element;

a first branch having a first constant thickness, a first branched end connected to said first end of said transverse part and a first free end opposite said first branched end at said proximal side; and a second branch having a second constant thickness, a second branched end connected to said second end of said transverse part and a second free end opposite said second branched end at said proximal side, said second constant thickness being identical to said first constant thickness wherein said transverse part, said first branch, and said second branch form a U-shape with a space between said first free end and said second free end, wherein said first free end is comprised of first projections facing toward said second branch and being within said first constant thickness, wherein said second free end is comprised of second projections facing toward said first branch and being within said second constant thickness; and a screw having threads and a diameter greater than said first constant thickness, wherein said screw is removably retained by said first projections and said second projections so as to protrude at least an even part of said threads outward from said first outer face and said second outer face along said first branch and along said second branch and complementarily anchor said element in the cavity by a screw tapped relationship, wherein said first branch is comprised of a first longitudinal groove facing outward from said element and away from said second branch, said first longitudinal groove being comprised of a first groove relief, and wherein said second branch is comprised of a second longitudinal groove facing outward from said element and away from said first branch, said second longitudinal groove is comprised of a second groove relief.

2. A system for performing posterior spinal arthrodesis at a facet joint, the system comprising:

the implant device being comprised of:

an element being comprised of:

a transverse part;

a first branch having a first constant thickness, a first branched end connected to said transverse part and a first free end opposite said first branched end; and a second branch having a second constant thickness, a second branched end connected to said second end of said transverse part and a second free end opposite said second branched end at said proximal side, said second constant thickness being identical to said first constant thickness wherein said transverse part, said first branch, and said second branch form a U-shape with a space between said first free end and said second free end, wherein said first free end is comprised of first projections facing toward said second branch and being within said first constant thickness, wherein said second free end is comprised of second projections facing toward said first branch and being within said second constant thickness; and a screw being removably retained by said first projections and said second projections so as to protrude at least an even part of said threads outward from said first outer face and said second outer face along said first branch and along said second branch and complementarily anchor said element in the cavity by a screw tapped relationship; and a positioning tool, wherein said positioning tool comprises:

a first part, having a first part back end and a first part tip end opposite said first part back end and being comprised of a first terminal end part at said first part tip end in removable holding engagement with said first branch outward from said element and away from said second branch and with said second branch outward from said element and away from said first branch;

a second part being coaxial with said first part and being in sliding engagement around said first part between said first part back end and said first terminal end part;

a third part, being inside said first part, having a third part back end and a third part free end opposite said third part back end, and being comprised of threaded hole at said third part free end in removable threaded engagement with said screw, said screw being positioned in said through hole so as to be removably retained by said first projections and said second projections, and a fourth part, being inside said third part and being comprised of a rod having a back rod end and a front rod end removably engaged with said screw so as to drive rotation of said screw through an action on said back rod end.

3. The system, according to claim 2, wherein said first terminal end part comprises two parallel branches.

4. The system, according to claim 2, wherein said first longitudinal groove is comprised of a first groove relief, wherein said second longitudinal groove is comprised of a second groove relief, wherein each parallel branch of said two parallel branch is comprised of a convex boss in removable friction fit engagement with a corresponding first groove relief or corresponding second groove relief, wherein each convex boss is in a locked configuration with the corresponding first groove relief or the corresponding second groove relief with said second part adjacent said first terminal end part.

5. The system, according to claim 4, wherein said first groove relief is comprised of a convex boss.

6. The system, according to claim 2, wherein said third part is tubular, and wherein said threaded hole is comprised of a cavity with a round, threaded cross-section.

7. The system, according to claim 3, wherein said positioning tool further comprises an additional part positioned outside said two parallel branches of said first part.

* * * * *